United States Patent [19]

Border

[11] Patent Number: 4,875,474

[45] Date of Patent: Oct. 24, 1989

[54] VARIABLE WALL THICKNESS INTERLOCKING INTRAMEDULLARY NAIL

[75] Inventor: Robert Border, Bourbon, Ind.

[73] Assignee: Biomet, Inc., Warsaw, Ind.

[21] Appl. No.: 150,025

[22] Filed: Jan. 29, 1988

[51] Int. Cl.⁴ .............................................. A61B 17/58
[52] U.S. Cl. ....................................... 128/92 Y; 72/367; 128/92 YZ; 128/92 YK
[58] Field of Search ............ 128/92 Y, 92 YZ, 92 YY, 128/92 YK, 92 YW, 92 YV, 92 YT, 92 YG, 92 YN

[56] References Cited

U.S. PATENT DOCUMENTS

| | | | |
|---|---|---|---|
| 2,136,471 | 11/1938 | Schneider | 128/92 R |
| 2,518,019 | 8/1950 | Kane | 128/92 R |
| 3,334,624 | 8/1967 | Schneider et al. | 128/92 R |
| 3,433,220 | 3/1969 | Zickel | 128/92 R |
| 3,977,398 | 8/1976 | Burstein | 128/92 YZ |
| 3,990,438 | 11/1976 | Pritchard | 128/92 YZ |
| 4,103,683 | 8/1978 | Neufeld | 128/92 YK |
| 4,212,683 | 7/1980 | Murphy | 437/26 |
| 4,341,206 | 7/1982 | Perrett et al. | 128/92 VD |
| 4,375,810 | 3/1983 | Belykh et al. | 128/92 R |
| 4,381,770 | 5/1983 | Neufeld | 128/92 YK |
| 4,423,721 | 1/1984 | Otte et al. | 128/92 VT |
| 4,446,857 | 5/1984 | Otte et al. | 128/92 YK |
| 4,457,301 | 7/1984 | Walker | 128/92 R |
| 4,475,545 | 10/1984 | Ender | 128/92 R |
| 4,622,959 | 11/1986 | Marcus | 128/92 YZ |
| 4,628,920 | 12/1986 | Mathys, Jr. et al. | 128/92 YZ |
| 4,697,585 | 10/1987 | Williams | 128/92 YZ |
| 4,776,330 | 10/1988 | Champman et al. | 128/92 YY |

FOREIGN PATENT DOCUMENTS

| | | |
|---|---|---|
| 902736 | 2/1982 | U.S.S.R. ..................... 128/92 YY |
| 1091921 | 5/1984 | U.S.S.R. ..................... 128/92 YY |
| 1593440 | 7/1981 | United Kingdom . |
| 2114005A | 8/1983 | United Kingdom . |

Primary Examiner—Robert A. Hafer
Assistant Examiner—Kevin G. Rooney
Attorney, Agent, or Firm—Barnes & Thornburg

[57] ABSTRACT

An intramedullary nail comprises a unitary piece of elongate material of tubular cross-section having variations in wall thickness along its length. The nail has a proximal portion, a distal portion and an intermediate portion between the proximal and distal portions. The wall thicknesses of the proximal and distal portions are substantially greater than the wall thickness of the intermediate portion. In preferred embodiments, the outside diameters of the proximal, intermediate and distal portions are substantially equal or, alternatively, the outside diameter of the proximal portion is larger than the substantially equal outside diameters of the distal and intermediate portions. The nail is provided with a longitudinal slot which preferably extends along substantially the entire length of the nail. The nail is also provided with transverse openings through the proximal and distal portions to receive interlocking screws, and a portion of the inside diameter of the proximal portion is threaded to provide a point of attachment for insertion and extraction devices. The invention further includes an advantageous method of making the nail from a single length of material, such as stainless steel tubing. The advantageous method includes the two-step process of machining the intermediate portion of the length of tubing to reduce the outside diameter and wall thickness thereof, while maintaining the inside diameter substantially constant, and swaging either the proximal portion or the distal portion (or both) to reduce the inside and outside diameters thereof, such that the wall thickness of the swaged portion is substantially greater than the wall thickness of the intermediate portion of the tubing. Another aspect of the invention is the provision of a cap for the internally threaded end of the proximal portion to prevent the ingrowth of tissue.

7 Claims, 3 Drawing Sheets

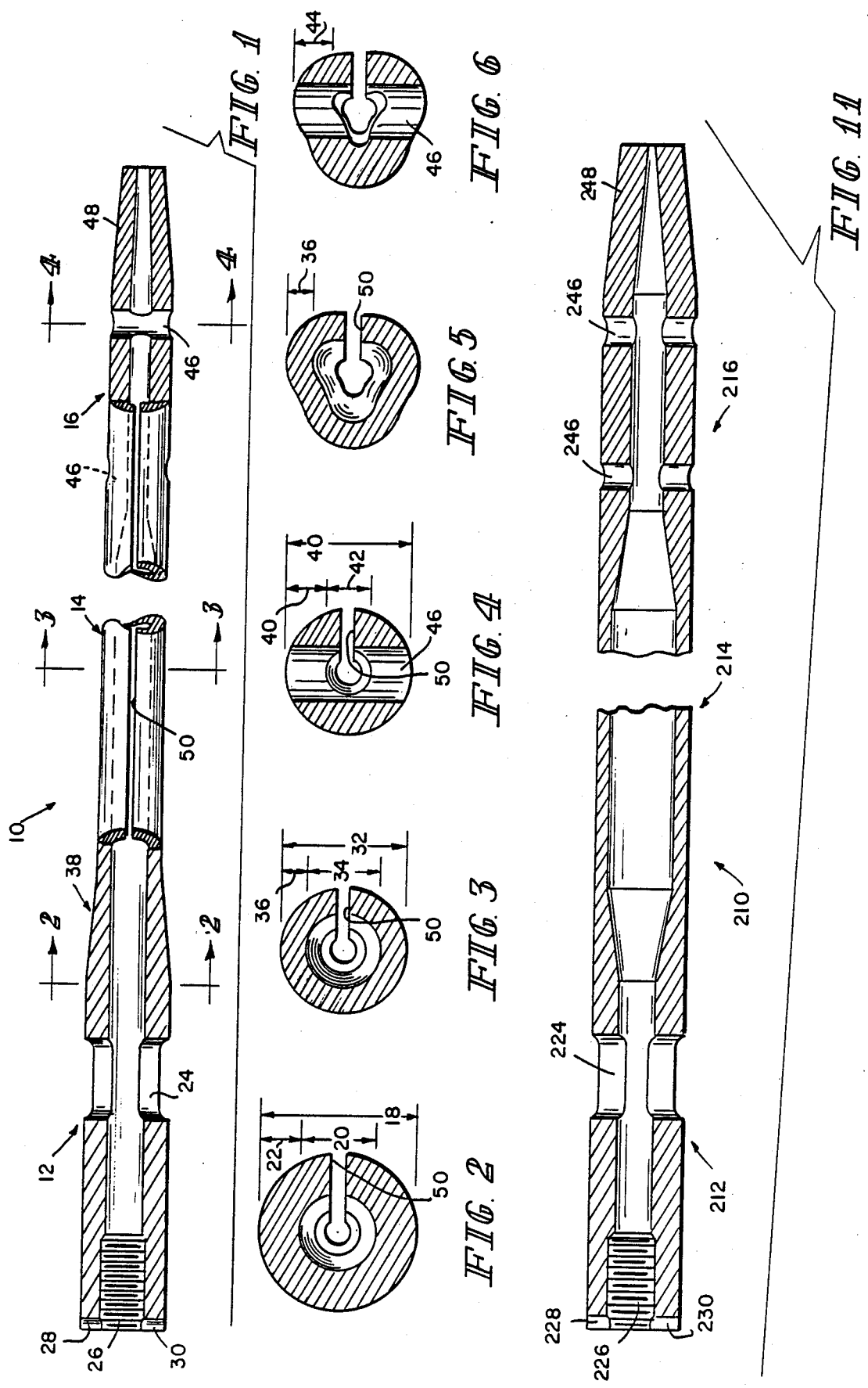

VARIABLE WALL THICKNESS INTERLOCKING INTRAMEDULLARY NAIL

BACKGROUND AND SUMMARY OF THE INVENTION

This invention relates generally to interlocking intramedullary nails and, more particularly, to a tubular interlocking intramedullary nail having variations in wall thickness along its length.

The use of intramedullary nailing in the treatment of fractures of the femur, tibia, and other "long" bones is well known. This practice can allow a fracture patient to resume limited use of the affected body part within days of the injury and subsequent surgery. The corresponding reduction in the amount of time during which the patient must be at least partially immobilized can drastically reduce the overall recovery period.

One of the earliest forms of intramedullary nails to achieve relative widespread acceptance and usage is often referred to as the Küntscher nail (or K-nail) for its developer Professor Gerhart Küntscher of Hamburg, Germany. The Küntscher nail is a slotted steel tube having a relatively thin side wall thickness which allows the nail to bend or flex slightly as it is driven into the somewhat curved medullary canal of a bone. The Küntscher nail is also transversely elastic and is approximately the same diameter as the medullary canal into which it is to be driven, causing the nail to be compressed against the sides of the canal and firmly locked in place by compressive forces acting along the length of the nail.

Despite the widespread success and acceptance of the Küntscher nail, it has been recognized that standard Küntscher nailing is contraindicated in the treatment of certain complex types of fractures. These fractures are often treated by dynamic or static locking of the nail on one or both ends by screws that extend transversely through the nail and into the major fragments of the fractured bone. This interlocking technique requires the provision of transverse holes or openings through the proximal and/or distal portions of the interlocked nail. Intramedullary nails rarely fail by stress fatigue when no interlocking screws are used. However, the transverse openings and screws of the interlocking nail produce the potential for high concentrations of stress at the proximal and distal ends of the nail, and numerous instances of fatigue failure of interlocking nails have been recorded and analyzed (see, for example "Fatigue Fracture of the Interlocking Nail in the Treatment of Fractures of the Distal Part of the Femoral Shaft" by R. W. Bucholz, M.D., S. E. Ross, M.S. and K. L. Lawrence, Ph.D, P.E., The Journal of Bone and Joint Surgery, Vol. 69-A, No. 9, December, 1987, pp. 1391–1399).

An object of the present invention is to provide an interlocking intramedullary nail which is more resistant to fatigue fractures in the proximal and distal portions of the nail.

Another object of the present invention is to provide an interlocking intramedullary nail which is not only resistant to fatigue fractures, but which retains the desirable flexibility and resilience of the standard Küntscher nail.

Yet another object of the present invention is to provide an especially advantageous method of manufacturing an interlocking intramedullary nail having the just-described desirable characteristics.

These and other objects of the invention are attained in an intramedullary nail having a proximal portion, a distal portion, and an intermediate portion between the proximal and distal portions, and having at least one opening extending transversely through at least one of either the proximal or distal portions. The nail comprises a unitary piece of elongate material of tubular cross-section having variations in wall thickness along its length. The wall thicknesses of the proximal and distal portions are substantially greater than the wall thickness of the intermediate portion. In an especially preferred embodiment, the wall thicknesses of the proximal and distal portions are approximately twice the thickness of those of the intermediate portion. In one preferred embodiment of the invention, the outside diameters of the distal and intermediate portions are substantially equal, while the outside diameter of the proximal portion is substantially larger. In an alternative embodiment, the outside diameters of the proximal, intermediate and distal portions are substantially equal. In especially preferred embodiments, the nail is provided with a longitudinal slot which extends along substantially the entire length of the nail, and the proximal end of the nail is provided with internal threads to provide for attachment of insertion and extraction devices. The substantially thicker cross-section of the proximal portion of the nail allows such features to be incorporated into the nail design, while maintaining the required strength and mechanical integrity to resist fatigue failure during use and to avoid problems during insertion and extraction.

Another aspect of the present invention relates to the provision of internal threads in the proximal end of the nail for attachment of insertion and extraction devices. It is not uncommon for intramedullary nails of the present type to remain within the body for a number of months, prior to being removed after the fractured bone has healed. During such extended periods, tissue growth around and into the threaded end portion of the nail can occur. Prior to removing the nail, it is necessary for the surgeon to remove such tissue growth to expose the internal threads to allow for attachment of an extraction tool. This is often done by cutting or drilling through the tissue that has grown into the nail, at the risk of damaging surrounding tissue, the nail end, or the internal threads. Accordingly, the nail of the present invention includes a threaded end cap whose function is to seal the end of the nail and the internal threads to prevent tissue ingrowth into these areas.

An especially advantageous method of making an intramedullary nail having variations in wall thickness along its length includes a two-step process to produce the basic overall shape of the nail. The process preferably begins with a single unitary length of tubing having a substantially constant inside diameter, outside diameter and wall thickness. For purposes of this discussion, the length of tubing can be said to have a proximal portion, a distal portion, and an intermediate portion between the proximal and distal portions. The first step in the preferred process is machining the intermediate portion of the length of tubing to reduce the outside diameter and wall thickness thereof, while maintaining the inside diameter substantially constant. The second step in the process is swaging either the proximal portion or the distal portion, or both, to reduce the inside and outside diameter(s) thereof, such that the wall thickness of the swaged portion of the tubing is substantially greater than the wall thickness of the intermediate portion of the tubing. As noted elsewhere in this application, one embodiment of the present invention is swaged such that the outside diameters of the proximal, intermediate, and distal portions are all substantially equal. An alternative embodiment results in a proximal portion which has a slightly larger outside diameter than do the intermediate and distal portions.

Additional machining steps may be performed on the distal and proximal portions of the tubing, either prior to or subsequent to the swaging step. Additional steps may also be performed to provide other features, such as the longitudinally extending slot, transverse openings, and internal threads in the proximal end of the tubing.

Although the preferred sequence of the two-step process is as illustrated in the figures described below, variations from this sequence which would produce substantially the same result are possible. Additionally, although the preferred method of manufacture begins with a single length of tubing, a single length of solid stock (or other material type) may also be used. If a single piece of solid stock is used, the machining step will include drilling at least a portion of the length of stock to produce a tubular cross-section in that portion, followed by the machining and swaging steps described above.

Other objects, advantages and novel features of the present invention will become apparent from the following detailed description of the invention when considered in conjunction with the accompanying drawings.

BRIEF DESCRIPTION OF THE DRAWINGS

FIG. 1 shows a cross-sectional view of an intramedullary nail according to the present invention.

FIG. 2 shows a sectional view taken along line 2—2 of FIG. 1.

FIG. 3 shows a cross-sectional view taken along line 3—3 of FIG. 1.

FIG. 4 shows a cross-sectional view taken along line 4—4 of FIG. 1.

FIG. 5 shows an alternative cross-sectional configuration taken along line 3—3 of FIG. 1.

FIG. 6 shows an alternative cross-sectional configuration taken along line 4—4 of FIG. 1.

FIGS. 7–11 illustrate the steps of the preferred method of manufacturing the intramedullary nail of the present invention.

DETAILED DESCRIPTION OF THE DRAWINGS

Figure 7:
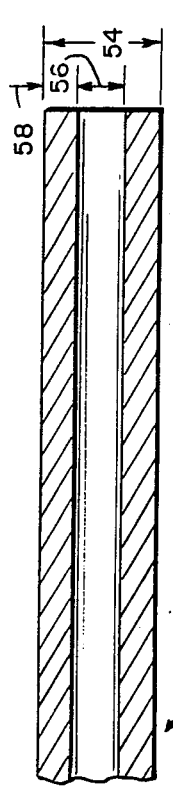

FIG. 1 shows a cross-sectional view of an intramedullary nail 10 constructed in accordance with the principles of the present invention. Nail 10 has at least three distinct regions or portions which, for purposes of this discussion, will be termed the proximal portion, generally indicated by reference numeral 12, the intermediate portion, generally indicated by reference numeral 14, and the distal portion, generally indicated by reference numeral 16.

Intramedullary nails of the type illustrated in FIG. 1 are typically produced in sizes which range from 8 mm to 20 mm (in 1 mm increments) in diameter, and from 20 cm to 52 cm in length. Nail 10 in FIG. 1 is typical of a nail in the smaller diameter size range (i.e., 8–13 mm) which is constructed in accordance with the present invention. As will be discussed below, larger nails may vary somewhat in overall configuration, specifically with regard to the outer diameter of the proximal portion, or head, of the nail.

Referring to FIG. 1, proximal portion 12 has a relatively large (as compared to the other portions) outside diameter 18 which is best illustrated in FIG. 2 which is a sectional view taken along line 2—2 of FIG. 1. Proximal portion 12 also has an inside diameter 20 and a wall thickness 22 which are discussed in more detail below in relation to similar features of the intermediate and distal portions 14 and 16.

Proximal portion 12 is further provided with a slot 24 which extends transversely through proximal portion 12. Slot 24 is provided to allow for passage of a screw or other fixation device, either perpendicularly or at an angle to the longitudinal axis of nail 10, after the nail has been placed in final position within the medullary canal of a fractured bone. Proximal portion 12 also has internal threads 26 extending from the end of nail 10 into proximal portion 12 for a relatively short distance. Threads 26 receive the threaded portion of an instrument used for inserting and/or extracting the nail from the medullary canal of a bone, as is generally illustrated in, for example, U.S. Pat. Nos. 3,334,624; 4,423,721 and 4,622,959. Also formed in the end of proximal portion 12 are two generally U-shaped grooves 28 and 30 which act as a guide for insertion and extraction tools, or for drill guides used in conjunction with installing fixation screws or fasteners, as is also illustrated in one or more of the above-noted patents.

Intermediate portion 14 has an outside diameter 32, an inside diameter 34, and a wall thickness 36, all of which are best illustrated in FIG. 3 which is a cross-sectional view taken along line 3—3 of FIG. 1. As can be seen in a comparison of FIGS. 2 and 3, outside diameter 32 of intermediate portion 14 is smaller than outside diameter 18 of proximal portion 12, while the respective inside diameters 34 and 20 are substantially equal. Wall thickness 36 of intermediate portion 14 is, accordingly, substantially smaller than wall thickness 22 of proximal portion 12. Between intermediate portion 14 and proximal portion 12 is a transition region 38 in which the outside diameter tapers from the relatively larger outside diameter 18 of proximal portion 12 to the relatively smaller outside diameter 32 of intermediate portion 14.

Distal portion 16 has an outside diameter 40, an inside diameter 42, and a wall thickness 44 which are best illustrated in FIG. 4 which is a cross-sectional view taken along line 4—4 of FIG. 1. Outside diameter 40 is substantially equal to outside diameter 32 of intermediate portion 14. However, inside diameter 42 of distal portion 16 is substantially smaller than inside diameter 34 of intermediate portion 14, and, accordingly, wall thickness 44 of distal portion 16 is substantially larger than wall thickness 36 of intermediate portion 14. In addition to these features, distal portion 16 is also provided with one or more transverse holes 46 for receiving bone screws or other fixation devices after nail 10 has been placed inside the medullary canal of a fractured bone. An end portion 48 of distal portion 16 may also be tapered to a point, if desired, in order to assist in insertion of the nail into the medullary canal.

An additional feature of nail 10 which is partially visible in FIG. 1, and which can be seen in each of FIGS. 2, 3 and 4, is slot 50 which is a longitudinally extending slot which preferably run the entire length of nail 10. As will be discussed below, the increased wall thickness in proximal portion 12 allows slot 50 to extend through the entire length of proximal portion 12, while lessening the possibility of proximal portion 12 "spreading" during the insertion and extraction process.

The varying dimensions of wall thicknesses 18, 32 and 40 are important considerations in the design of the nail of the present invention. Typical wall thicknesses for the 13 mm nail illustrated in FIG. 1 are 0.118 inch for wall thickness 22 (the proximal portion), 0.059 inch for wall thickness 36 (the intermediate portion), and 0.098 inch for wall thickness 44 (the distal portion). It should be noted that the wall thicknesses 22 and 44 are approximately double that of wall thickness 36. However, nail 10 is formed of a single piece of tubing which has no welds or other joints at which weaknesses or defects might occur.

The relatively thin wall thickness 36 in intermediate portion 14 allows nail 10 to retain an appropriate degree of flexibility which allows it to bend in conformance with the shape of the medullary canal into which it is inserted, and provides for a degree of tortional flexibility. The relatively thick wall thicknesses 22 and 44 of proximal and distal portions 12 and 16 provide extra strength in the areas through which slot 24 and holes 46 extend. These openings produce weaknesses in the nail and very often define the location at which fatigue failure (i.e., breakage) will occur. To maintain this relatively thick wall thickness throughout the length of the nail would result in a decrease in the desired flexibility of the central portion of the nail. By forming the nail with substantially greater wall thicknesses in proximal and distal portions 12 and 16, these portions are strengthened without adversely impacting upon overall nail flexibility. An additional advantage to this arrangement is that longitudinal slot 50 can be extended all the way through and to the end of Proximal portion 12 with less fear that this portion of the nail will "spread" or open under the pressure of insertion or extraction, or as a result of over-insertion of an instrument used for nail insertion or extraction.

FIGS. 5 and 6 show alternative cross-sectional embodiments taken along lines 3—3 and 4—4 of FIG. 1, respectively. These figures depict a cloverleaf cross-sectional shape which is preferably swaged into intermediate portion 14 and distal portion 16 of nail 10 during the manufacturing process. This shape better defines and concentrates the areas of contact between the outside of the nail and the bone tissue, and is generally preferred over other cross-sectional shapes that may be used.

FIGS. 7-11 illustrate an especially advantageous two-step process which forms an important part of the overall method of manufacturing the nail of the present invention. The two steps of this process include a machining step and a swaging step, each of which is described in detail below.

FIG. 7 shows a length of tubing 52 which has a relatively uniform outside diameter 54, a relatively uniform inside diameter 56, and a relatively uniform wall thickness 58. Tubing 52 is a single, unitary section of tubing which has no joints, welds, or other features which might provide a likely location for a weakness or defect. Tubing 52 is preferably made from stainless steel, although other biocompatible materials such as titanium, titanium alloys, or fiberreinforced non-metallic materials, could be used.

Figure 8:
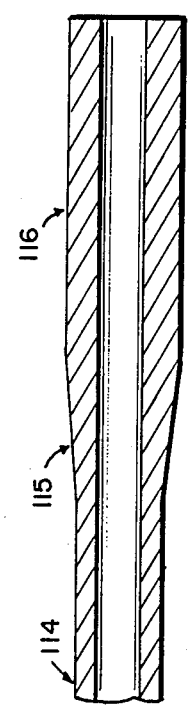

FIG. 8 shows tubing 52 following a machining step in which the wall thickness of intermediate portion 114 has been reduced. On either end of intermediate portion 114, transition zones 115 and 138 are provided in which the outside diameter of tubing 52 tapers between the original diameter and the newly machined outside diameter of intermediate portion 114. If desired, proximal portion 112 and distal portion 116 of tubing 52 may also be machined during this step of the manufacturing process. However, the amount of material removed from the outside diameters of these portions would be less, so that the outer diameter of intermediate portion 114 and, correspondingly, the wall thickness of portion 114 are substantially smaller than the outer diameters and wall thicknesses of proximal and distal portions 112 and 116, respectively, after the machining step is complete.

It should be noted at this point that, although the "starting point" for manufacture of the nail as illustrated in FIGS. 7-11 is a length of tubing, the method of the present invention is not intended to be strictly limited to the use of tubing. For example, a length of solid stock can also be used. In that case, the machining step would include boring (or "gun-drilling") the stock, prior to reducing the outside diameter of the intermediate portion. The use of tubing is preferred when stainless steel or other materials readily available in tubing form is used for the nail of the present invention. However, certain materials, such as titanium, may not be as readily available, or may be prohibitively expensive, in tubing form.

Figure 9:
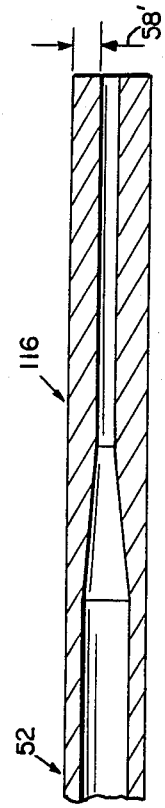

FIG. 9 shows tubing 52 of FIGS. 7 and 8 after a swaging step in which the outside diameter of distal portion 116 has been reduced and made approximately equal to the outside diameter of intermediate portion 114. The inside diameter of distal portion 16 is reduced during the swaging process, and the wall thickness 58' of portion 116 is maintained, or slightly increased, as compared to the wall thickness of the original tubing. The length of distal portion 116 may also be increased slightly by the swaging process.

Figure 10:
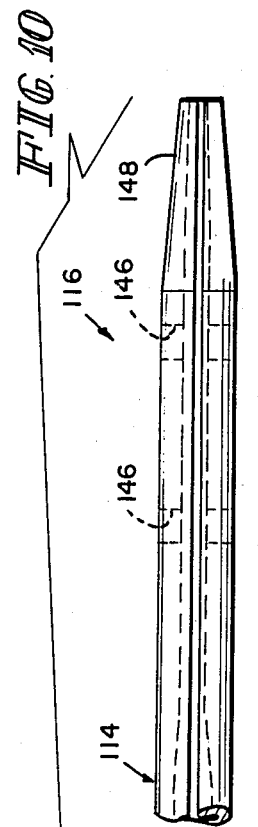

FIG. 10 shows the tubing of FIGS. 7, 8 and 9 after intramedullary nail 110 has been substantially completed. Slotted opening 124 has been provided through the relatively thick walls of proximal portion 112, and holes 146 have been similarly provided through the relatively thick walls of distal portion 116. Internal threads 126 have been provided in the end of proximal portion 112. An elongated slot 150 has also been provided by a machining operation, and extends along the entire length of nail 110. Grooves 128 and 130 are also provided in the end of proximal portion 112 to mate with and guide appropriate fixtures and instruments Additional finishing steps to complete the nail include polishing, swaging to obtain the cloverleaf cross-section (if desired), and tapering the tip end of distal portion 116.

It should be noted that the sequence of the machining and swaging operations is not critical (i.e., the swaging operation to distal portion 116 could be performed prior to machining intermediate portion 114). Although the sequence described is the preferred mode of manufacture, and represents the best mode of practicing the invention as presently understood by Applicant, it should be clearly understood that the claims which follow below are not intended to be limited to this preferred sequence.

FIG. 11 shows an intramedullary nail 210 which is at the same stage of completion as nail 110 of FIG. 10. Nail 210 is typical of a nail in the larger diameter size range (14–20mm) which is constructed in accordance with the present invention. Nail 210 differs from nail 110 in that the outer diameter of proximal portion 212 is substantially equal to the outside diameters of intermediate and distal portions 214 and 216. The inside diameter of proximal portion 212 is substantially smaller than the inside diameter of intermediate portion 214. This structure is obtained by swaging proximal portion 212 (or, alternatively, the entire length of nail 210), as well as distal portion 216.

Figure 12:
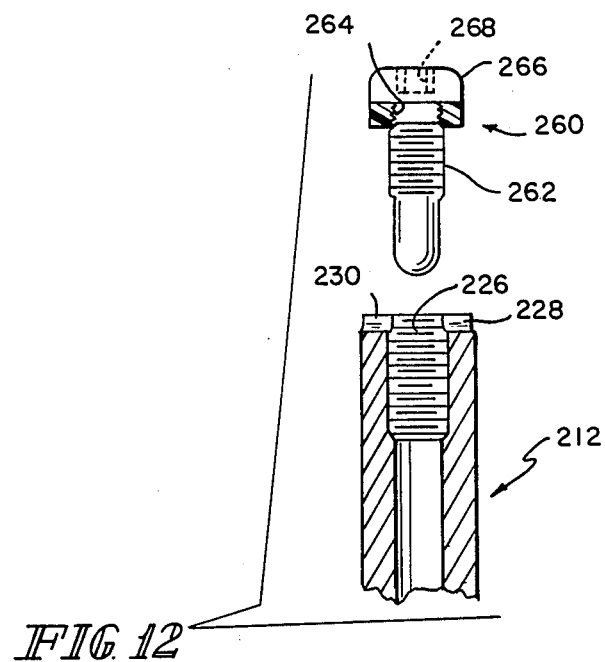
FIG. 12 shows a side view of an end cap used for sealing the proximal end of the intramedullary nail of the present invention to prevent tissue ingrowth.

FIG. 12 shows an end part of proximal portion 212 positioned to receive end cap 260. End cap 260 comprises an elongate threaded portion 262 which is substantially equal in length to internal threads 226 provided in the end of proximal portion 212. A seal or washer 264 is provided to form a seal between the bottom surface of head 266 of end cap 260 and the end of proximal portion 212. Washer 264 also acts to lock or secure end ca 260 in position after it has been threaded into proximal portion 212. Means for attaching or receiving a tool for turning end cap 260 are provided in head 266. In the embodiment illustrated in FIG. 12, hexagonally-shaped recess 268 is provided for this purpose.

After intramedullary nail 210 has been positioned within, for example, a fractured femur, end cap 260 is used to seal the end of proximal portion 212 and internal threads 226. This prevents the ingrowth of cartilage or other types of tissue into the end of nail 210, and in proximity to threads 226. When, at a future date, the nail is to be removed, end cap 260 is first removed from proximal portion 212 to expose the end of the nail and internal threads 226 in an undamaged condition.

End cap 260 can be formed of the same material used to form the associated nail (e.g., stainless steel, titanium or titanium alloy, etc.) or of any other biologically compatible material. Although like metals are preferred when selecting materials for use with metal nails, plastics (such as UHMWPE) may also be employed in making the end cap.

Although use of end cap 260 is considered to be advantageous with the nails depicted in FIGS. 1–11 of the present application, such advantageous use is not limited to nails which incorporate all the features of these particular designs. End cap 260 can be used to like advantage in other nails which incorporate internal threads in the proximal end portion, or nails which would otherwise benefit from the provision of a seal in the proximal end of the nail (whether or not threads are provided) to prevent the ingrowth of tissue during the implantation period. Accordingly, the applicability of this aspect of the present invention is to be limited only by the scope of the associated claims.

For purposes of this application, the term "swage" or "swaging" is not intended to refer to any one particular metal forming technique, but rather to any of a number of techniques which may be deemed suitable by those of ordinary skill in metal forming to accomplish the results described. Acceptable techniques might also be referred to as "forging" techniques.

Although the intramedullary nail illustrated and discussed in detail above is especially well-suited for treating fractures of the femur, the present invention is not limited to that specific application. The principles and features discussed are equally applicable to nails used for treating fractures of the tibia, and for fractures of other long bones commonly treated (or amenable to treatment) by nailing techniques.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An intramedullary nail, comprising a proximal portion, a distal portion and an intermediate portion between the proximal and distal portions, and having at least one opening extending transversely through at least one of said proximal and distal portions, said nail being formed of a unitary piece of elongate material of tubular cross-section having variations in wall thickness along its length, wherein the wall thicknesses of the proximal and distal portions are substantially greater than the wall thickness of the intermediate portion.

2. An intramedullary nail according to claim 1, wherein the wall thickness of the proximal and distal portions are approximately twice the wall thickness of said intermediate portion.

3. An intramedullary nail according to claim 1, wherein the outside diameters of said distal and intermediate portions are substantially equal along at least a substantial part of said portions.

4. An intramedullary nail according to claim 1, wherein the outside diameters of said proximal, intermediate and distal portions are substantially equal.

5. An intramedullary nail according to claim 1, wherein the nail is provided with a longitudinal slot which extends along substantially the entire length of the nail.

6. An intramedullary nail according to claim 1, wherein a portion of an inside diameter of the proximal portion is threaded to provide a point of attachment for insertion and extraction devices.

7. An intramedullary nail according to claim 6, further comprising an end cap for sealing the threaded portion of the proximal portion after insertion of the nail into a medullary canal of a bone.

* * * * *